US011420075B2

(12) United States Patent
Chen et al.

(10) Patent No.: US 11,420,075 B2
(45) Date of Patent: Aug. 23, 2022

(54) SYSTEM AND METHOD FOR RECONSTRUCTING IMAGE VOLUMES FROM SPARSE TWO-DIMENSIONAL PROJECTION DATA

(71) Applicant: Wisconsin Alumni Research Foundation, Madison, WI (US)

(72) Inventors: Guang-Hong Chen, Madison, WI (US); Juan Camilo Montoya, Madison, WI (US); Thomas M. Grist, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 515 days.

(21) Appl. No.: 16/577,164

(22) Filed: Sep. 20, 2019

(65) Prior Publication Data

US 2020/0094074 A1 Mar. 26, 2020

Related U.S. Application Data

(60) Provisional application No. 62/734,960, filed on Sep. 21, 2018.

(51) Int. Cl.
*A61B 6/00* (2006.01)
*A61N 5/10* (2006.01)
(Continued)

(52) U.S. Cl.
CPC ............ *A61N 5/1037* (2013.01); *A61B 6/032* (2013.01); *A61B 6/4028* (2013.01); *A61B 6/4417* (2013.01); *A61B 6/466* (2013.01); *A61B 6/482* (2013.01); *A61B 6/487* (2013.01); *A61B 6/5223* (2013.01); *A61B 6/5235* (2013.01);
(Continued)

(58) Field of Classification Search
CPC .... G06T 11/003; G06T 11/005; G06T 11/006; G06T 11/008; A61N 5/103; A61N 5/1031; A61B 6/032; A61B 6/5223
See application file for complete search history.

(56) References Cited

U.S. PATENT DOCUMENTS

2019/0251713 A1 8/2019 Chen

OTHER PUBLICATIONS

Chen, G.-H., et al. "Time-resolved interventional cardiac C-arm cone-beam CT: An application of the PICCS algorithm." IEEE transactions on medical imaging 31.4 (2011): 907-923.
(Continued)

*Primary Examiner* — Dani Fox
(74) *Attorney, Agent, or Firm* — Quarles & Brady LLP

(57) ABSTRACT

A system and method for acquiring medical images of a subject includes performing two-dimensional (2D) scan of a subject using a medical imaging system to acquire 2D data from at least two view angles and generating a three-dimensional (3D) model of the subject from the 2D data. The method also includes extracting desired images of the subject from the 3D model. The desired images are at view angles different from the at least two view angles. The method further includes prescribing an imaging study of the subject using the desired images of the subject to control at least one of a signal-to-noise ratio of data acquired using the imaging study or a dose of ionizing radiation delivered to the subject during the imaging study. The method also includes performing the imaging study using the medical imaging system to acquire imaging data from the subject and reconstructing images of the subject from the imaging data.

17 Claims, 13 Drawing Sheets

(51) Int. Cl.
   *G06T 11/00* (2006.01)
   *G06T 15/08* (2011.01)
   *G06T 15/20* (2011.01)
   *A61B 6/03* (2006.01)
   *G06T 17/00* (2006.01)

(52) U.S. Cl.
   CPC ............ *A61B 6/5258* (2013.01); *A61B 6/542* (2013.01); *G06T 11/005* (2013.01); *G06T 11/006* (2013.01); *G06T 15/08* (2013.01); *G06T 15/20* (2013.01); *G06T 17/00* (2013.01); *G06T 2210/41* (2013.01)

(56) References Cited

OTHER PUBLICATIONS

Kingma D. et al., "Adam: A method for stochastic optimization," arXiv preprint arXiv:1412.6980, 2014.

Li, K. et al., "Statistical model based iterative reconstruction (MBIR) in clinical CT systems: Experimental assessment of noise performance," Medical physics 41(4), p. 041906, 2014.

Pickhardt, P.J. et al., "Abdominal CT with model-based iterative reconstruction (MBIR): initial results of a prospective trial comparing ultralow-dose with standard-dose imaging," American journal of roentgenology 199(6), pp. 1266-1274, 2012.

Pooler, B. D. et al., "Prospective Evaluation of Reduced Dose Computed Tomography for the Detection of Low-Contrast Liver Lesions: Direct Comparison with Concurrent Standard Dose Imaging," European Radiology, pp. 1-12, 2016.

Qi, Z. et al. "Extraction of tumor motion trajectories using PICCS-4DCBCT: A validation study." Medical physics 38.10 (2011): 5530-5538.

SYSTEM AND METHOD FOR RECONSTRUCTING IMAGE VOLUMES FROM SPARSE TWO-DIMENSIONAL PROJECTION DATA

CROSS-REFERENCE TO RELATED APPLICATIONS

This application is based on, claims priority to, and incorporate herein by reference 62/734,960, filed Sep. 21, 2018, and entitled "SYSTEM AND METHOD FOR RECONSTRUCTING IMAGE VOLUMES FROM SPARSE TWO-DIMENSIONAL PROJECTION DATA."

STATEMENT REGARDING FEDERALLY SPONSORED RESEARCH

This invention was made with government support under EB021183 awarded by the National Institutes of Health. The government has certain rights in the invention.

BACKGROUND

The present disclosure relates to systems and methods for medical image data preparation, acquisition, and/or reconstruction. More particularly, systems and method are provided for generating medical images with greater efficiency, less artifacts, and/or greater information and flexibility than traditional techniques used with imaging systems, such as computed tomography (CT) imaging systems.

With conventional image reconstruction techniques, such as filtered backprojection for multi-detector CT (MDCT), C-arm cone beam CT (CBCT) imaging, on-board cone beam CT for image guidance in stereotactic body radiation therapy (SBRT) and radiation surgery such as gamma knife, individual images are reconstructed from a corresponding set of data acquired with the medical imaging system. For example, one image is reconstructed from a single sinogram in x-ray MDCT, CBCT imaging. The dominant framework for CT image reconstruction is filtered backprojection (FBP). Though well-understood and widely-adopted, FBP suffers from some inherent limitations and, thus, many efforts have been made to control the shortcomings of traditional CT hardware and the reconstruction of FBP.

For example, to monitor tumor motion in radiation therapy and radiosurgery, two x-ray source-detector assemblies are used in fluoroscopy data acquisition mode to acquire two separate views of two-dimensional (2D) x-ray fluoroscopy images. The tumor motion pattern or fiducial marker motion profile is then estimated from the acquired two individual 2D fluoroscopic images series. Due to the unavailability of gantry motion or slow mechanical gantry motion in data acquisitions, the desired cone beam CT fluoroscopic image volumes cannot be obtained for tumor motion extraction and patient positioning for high precision treatment requirement in radiosurgery and stereotactic body radiation therapy (SBRT).

For another example, the ionizing radiation delivered to patients during MDCT imaging has been shown to be a potential mechanism of carcinogenesis. Hence, many have worked to develop hardware, software, and imaging protocols to lower radiation dose, while still maintaining the image quality required for clinical analysis. X-ray tube current reduction is considered as one practical way to reduce the radiation dose. However, a reduction in detected x-ray fluence lowers the signal-to-noise ratio in the projection data and, thus, increases the noise in the reconstructed images, if conventional FBP is used for reconstruction.

One common example of the complexities of managing dose, signal, and clinical need for information is reflected in the use of scout scans as a precursor to a fully 3D MDCT imaging study. That is, 2D scout scans are often utilized as a planning step that is performed before undertaking a 3D MDCT imaging study and even MR imaging studies. Such scout scans typically include an anterior/posterior (A/P) view and a lateral view. Thus, two, 2D images taken from transverse view angles are provided and used to prescribe the 3D imaging study. Unfortunately, 2D scout scans do not provide sufficiently detailed information about interactions between x-rays and subjects and often leads to erroneous information for patient positioning, scan parameter prescription, and finally the radiation dose delivery. Furthermore, some have attempted to use these 2D scout scans as a tool to perform dose control during the 3D imaging, such as to reduce or control dose based on anatomical information determined from the 2D scout scans. However, the limited information available from two 2D images makes sophisticated dose control very difficult and dependent upon assumptions that can inject yet further errors into the dose control efforts. Of course, increasing the number of views or imaging data acquired when performing the scout scans undermines the very dose control that is desired, by subjecting the patient to additional dose from the scout scan before even beginning the 3D or higher-resolution imaging study that is to be prescribed using the 2D scout scan.

Thus, it would be desirable to have improved systems and methods to assist with managing signal-to-noise ratio and, in CT imaging, its relation to dose prescription/control.

SUMMARY

In accordance with one aspect of the disclosure, a method for acquiring four-dimensional (4D) medical images of a subject is provided that includes performing 2D fluoroscopic x-ray imaging of subject using a medical imaging system to acquire 2D fluoroscopic projection image data from two x-ray fluoroscopic image devices located to simultaneously acquire x-ray fluoroscopic images of subjects. The method can also include extracting motion profile of the subject from the 4D subject model.

In accordance with one aspect of the disclosure, a method for acquiring medical images of a subject is provided that includes performing two-dimensional (2D) scout scan of a subject using a medical imaging system to acquire 2D data from at least two view angles and generating a three-dimensional (3D) model of the subject from the 2D data. The method also includes extracting desired images of the subject from the 3D model. The desired images are at view angles different from the at least two view angles. The method further includes prescribing an imaging study of the subject using the desired images of the subject to control at least one of a signal-to-noise ratio of data acquired using the imaging study or a dose of ionizing radiation delivered to the subject during the imaging study. The method also includes performing the imaging study using the medical imaging system to acquire imaging data from the subject and reconstructing images of the subject from the imaging data.

In accordance with another aspect of the disclosure, a computed tomography (CT) system is provided that includes an x-ray source and associated detectors configured to acquire imaging data from a subject over a range of view angles. The system also includes a computer system including at least one processor configured to cause the x-ray source and associated detectors to acquire two-dimensional (2D) localizer images of a subject at least two view angles and generate a three-dimensional (3D) model of the subject from the 2D localizer images. The computer system is further configured to extract desired images of the subject from the 3D model, wherein the desired images are at view angles different from the at least two view angles and prescribe an imaging study of the subject using the desired images of the subject to control a dose of ionizing radiation delivered to the subject by the x-ray source during the imaging study. The computer system is also configured to cause the x-ray source and associated detectors to perform the imaging study to acquire imaging data from the subject and reconstruct images of the subject from the imaging data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
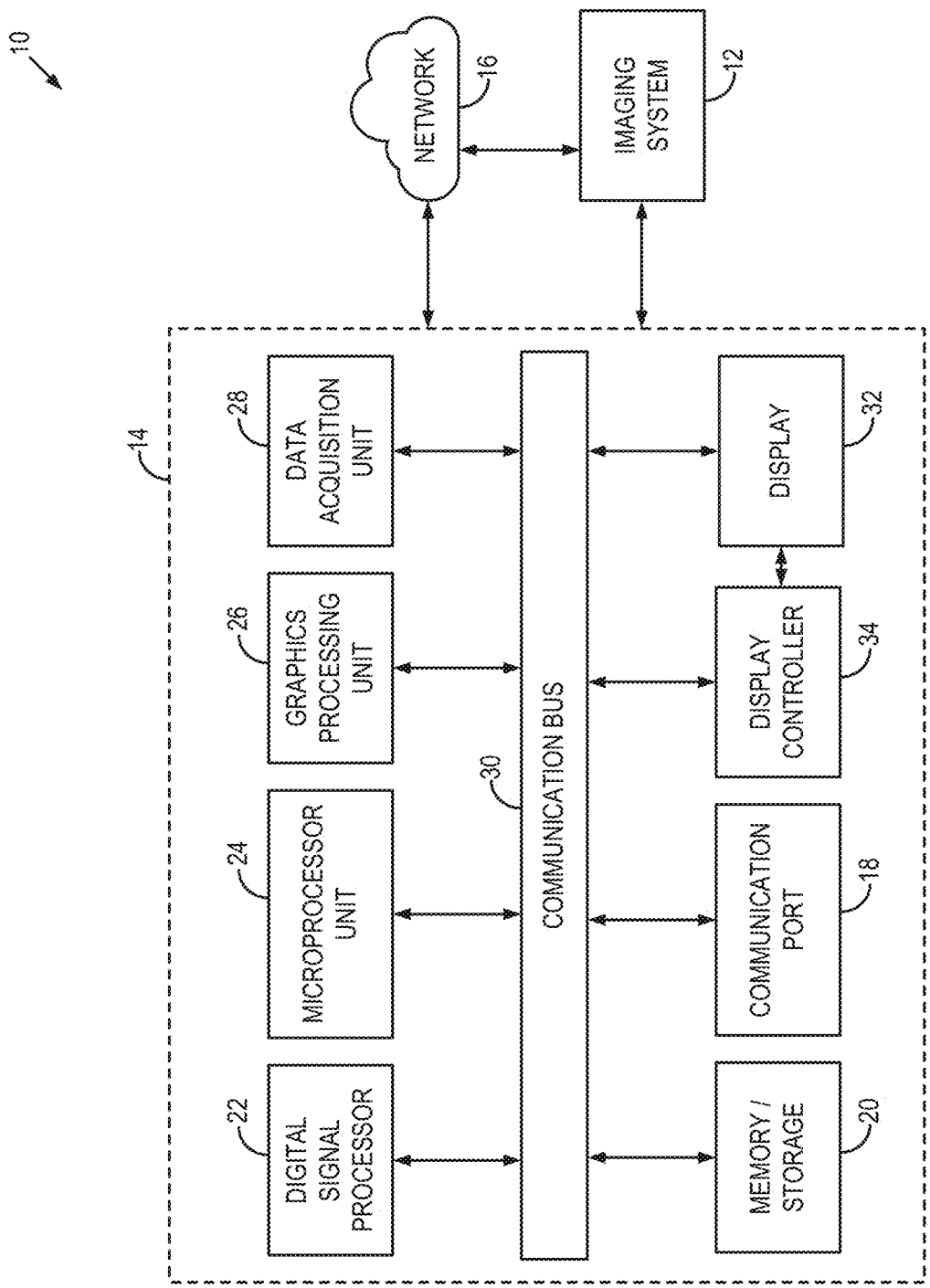
FIG. 1 is a schematic diagram of an example computer system that can be configured to implement the methods described herein.

Referring now to FIG. 1, a block diagram of an example system 10 is provided that can be configured to carry out techniques, methods, and processes accordance with the present disclosure. The system may include an imaging system 12 that is coupled to a computer system 14. The coupling of the imaging system 12 to the computer system 14 may be a direct or dedicated network connection, or may be through a broad network 16, such as an intranet or the Internet.

The computer system 14 may be a workstation integrated with or separate from the medical imaging systems 12 or a variety of other medical imaging systems, including, as non-limiting examples, computed tomography (CT) system, magnetic resonance imaging (MRI) systems, positron emission tomography (PET) systems, single photon emission computed tomography (SPECT) systems, and the like. Furthermore, the computer system 14 may be a workstation integrated within the medical imaging system 12 or may be a separate workstation or mobile device or computing system. To this end, the following description of particular hardware and configurations of the hardware of the example computer system 14 is for illustrative purposes. Some computer systems may have varied, combined, or different hardware configurations.

Medical imaging data acquired by the medical imaging system 12 or other imaging system can be provided to the computer system 14, such as over the network 16 or from a storage device. To this end, the computer system 14 may include a communications port or other input port 18 for communication with the network 16 and system coupled thereto. Also, the computer system 14 may include memory and storage capacity 20 to store and access data or images.

In some configuration, computer system 14 may include one or more processing systems or subsystems. That is, the computer system 14 may include one or more physical or virtual processors. As an example, the computer system 14 may include one or more of a digital signal processor (DSP) 22, a microprocessor unit (MPU) 24, and a graphics processing unit (GPU) 26. If the computer system 14 is integrated into the medical imaging system, a data acquisition unit 28 may be connected directly to the above-described processor(s) 22, 24, 26 over a communications bus 30, instead of communicating acquired data or images via the network 16. As an example, the communication bus 30 can be a group of wires, or a hardwire used for switching data between the peripherals or between any component, such as the communication buses described above.

The computer system 14 may also include or be connected to a display 32. To this end, the computer system 14 may include a display controller 34. The display 32 may be a monitor connected to the computer system 14 or may be integrated with the computer system 14, such as in portable computers or mobile devices.

Figure 2A:
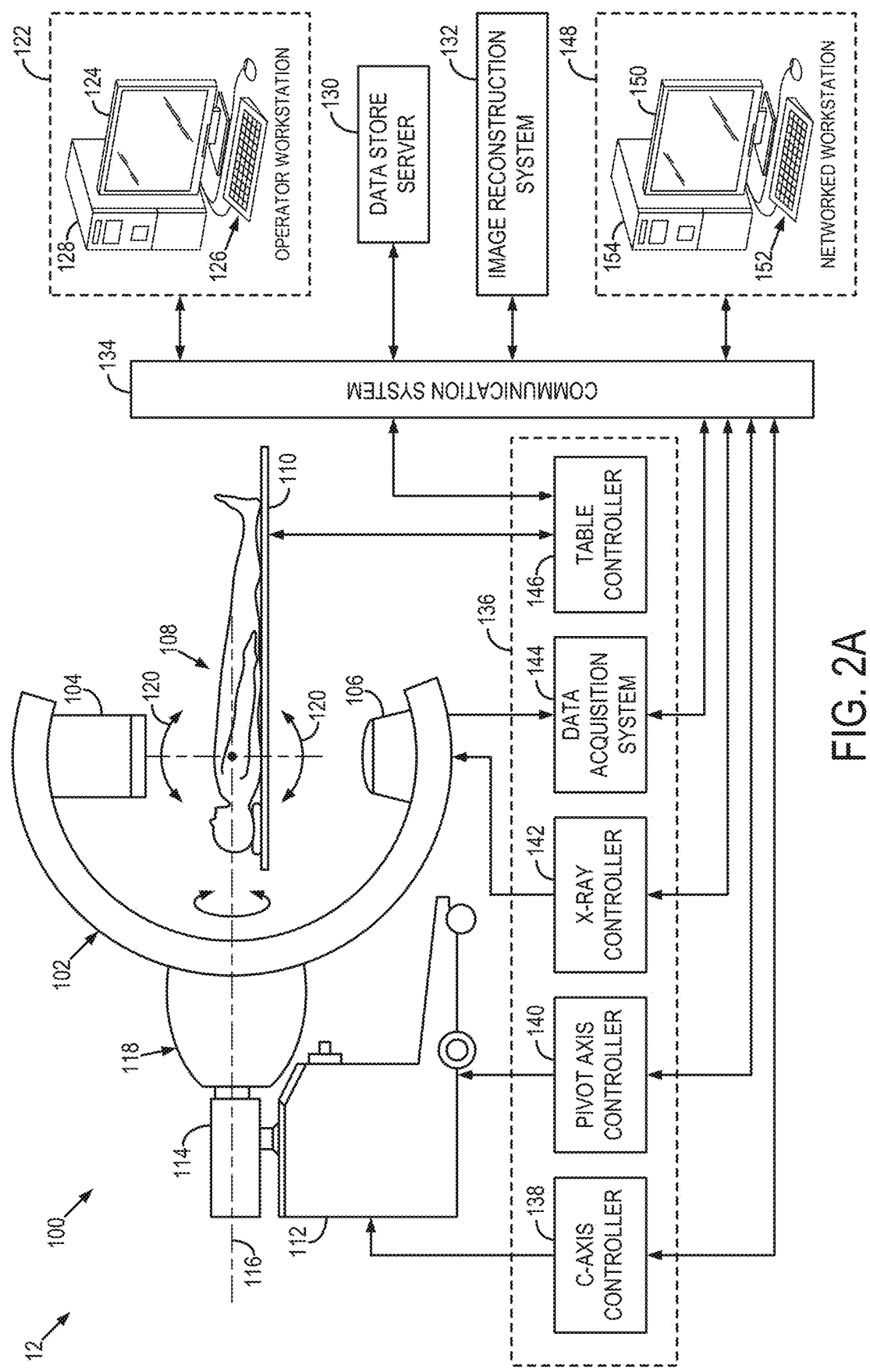
FIG. 2A is a schematic diagram of a C-arm x-ray computed tomography (CT) imaging system configured in accordance with the present disclosure.
Figure 2B:
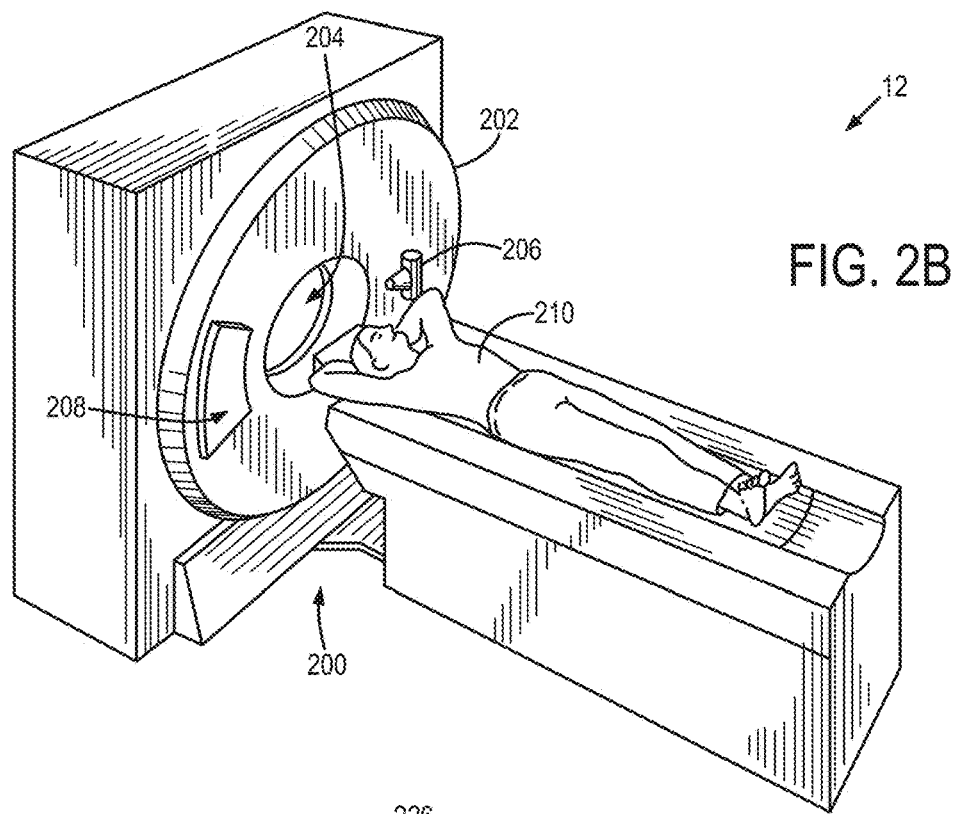
FIG. 2B is a perspective view of an example of an x-ray computed tomography (CT) system.

Referring to FIG. 2A, one, non-limiting example of the imaging system 12 of FIG. 1 is provided. Specifically, in this example, a so-called "C-arm" x-ray imaging system 100 is illustrated for use in accordance with some aspects of the present disclosure. Such an imaging system is generally designed for use in connection with interventional procedures. Such systems stand in contrast to, for example, traditional computed tomography (CT) systems 200, such as illustrated in FIG. 2B, which may also serve as an example of the imaging system 12 of FIG. 1.

Referring again to FIG. 2A, the C-arm x-ray imaging system 100 includes a gantry 102 having a C-arm to which an x-ray source assembly 104 is coupled on one end and an x-ray detector array assembly 106 is coupled at its other end. The gantry 102 enables the x-ray source assembly 104 and detector array assembly 106 to be oriented in different positions and angles around a subject 108, such as a medical patient or an object undergoing examination, which is positioned on a table 110. When the subject 108 is a medical patient, this configuration enables a physician access to the subject 108.

The x-ray source assembly 104 includes at least one x-ray source that projects an x-ray beam, which may be a fan-beam or cone-beam of x-rays, towards the x-ray detector array assembly 106 on the opposite side of the gantry 102. The x-ray detector array assembly 106 includes at least one x-ray detector, which may include a number of x-ray detector elements. Examples of x-ray detectors that may be included in the x-ray detector array assembly 106 include flat panel detectors, such as so-called "small flat panel" detectors. Such a detector panel allows the coverage of a field-of-view of approximately twelve centimeters.

Together, the x-ray detector elements in the one or more x-ray detectors housed in the x-ray detector array assembly 106 sense the projected x-rays that pass through a subject 108. Each x-ray detector element produces an electrical signal that may represent the intensity of an impinging x-ray beam and, thus, the attenuation of the x-ray beam as it passes through the subject 108. In some configurations, each x-ray detector element is capable of counting the number of x-ray photons that impinge upon the detector. During a scan to acquire x-ray projection data, the gantry 102 and the components mounted thereon rotate about an isocenter of the C-arm x-ray imaging system 100.

The gantry 102 includes a support base 112. A support arm 114 is rotatably fastened to the support base 112 for rotation about a horizontal pivot axis 116. The pivot axis 116 is aligned with the centerline of the table 110 and the support arm 114 extends radially outward from the pivot axis 116 to support a C-arm drive assembly 118 on its outer end. The C-arm gantry 102 is slidably fastened to the drive assembly 118 and is coupled to a drive motor (not shown) that slides the C-arm gantry 102 to revolve it about a C-axis, as indicated by arrows 120. The pivot axis 116 and C-axis are orthogonal and intersect each other at the isocenter of the C-arm x-ray imaging system 100, which is indicated by the black circle and is located above the table 110.

The x-ray source assembly 104 and x-ray detector array assembly 106 extend radially inward to the pivot axis 116 such that the center ray of this x-ray beam passes through the system isocenter. The center ray of the x-ray beam can thus be rotated about the system isocenter around either the pivot axis 116, the C-axis, or both during the acquisition of x-ray attenuation data from a subject 108 placed on the table 110. During a scan, the x-ray source and detector array are rotated about the system isocenter to acquire x-ray attenuation projection data from different angles. By way of example, the detector array is able to acquire thirty projections, or views, per second.

The C-arm x-ray imaging system 100 also includes an operator workstation 122, which typically includes a display 124; one or more input devices 126, such as a keyboard and mouse; and a computer processor 128. The computer processor 128 may include a commercially available programmable machine running a commercially available operating system. The operator workstation 122 provides the operator interface that enables scanning control parameters to be entered into the C-arm x-ray imaging system 100. In general, the operator workstation 122 is in communication with a data store server 130 and an image reconstruction system 132. By way of example, the operator workstation 122, data store sever 130, and image reconstruction system 132 may be connected via a communication system 134, which may include any suitable network connection, whether wired, wireless, or a combination of both. As an example, the communication system 134 may include both proprietary or dedicated networks, as well as open networks, such as the Internet.

The operator workstation 122 is also in communication with a control system 136 that controls operation of the C-arm x-ray imaging system 100. The control system 136 generally includes a C-axis controller 138, a pivot axis controller 140, an x-ray controller 142, a data acquisition system (DAS) 144, and a table controller 146. The x-ray controller 142 provides power and timing signals to the x-ray source assembly 104, and the table controller 146 is operable to move the table 110 to different positions and orientations within the C-arm x-ray imaging system 100.

The rotation of the gantry 102 to which the x-ray source assembly 104 and the x-ray detector array assembly 106 are coupled is controlled by the C-axis controller 138 and the pivot axis controller 140, which respectively control the rotation of the gantry 102 about the C-axis and the pivot axis 116. In response to motion commands from the operator workstation 122, the C-axis controller 138 and the pivot axis controller 140 provide power to motors in the C-arm x-ray imaging system 100 that produce the rotations about the C-axis and the pivot axis 116, respectively. For example, a program executed by the operator workstation 122 generates motion commands to the C-axis controller 138 and pivot axis controller 140 to move the gantry 102, and thereby the x-ray source assembly 104 and x-ray detector array assembly 106, in a prescribed scan path.

The DAS 144 samples data from the one or more x-ray detectors in the x-ray detector array assembly 106 and converts the data to digital signals for subsequent processing. For instance, digitized x-ray data is communicated from the DAS 144 to the data store server 130. The image reconstruction system 132 then retrieves the x-ray data from the data store server 130 and reconstructs an image therefrom. The image reconstruction system 130 may include a commercially available computer processor, or may be a highly parallel computer architecture, such as a system that includes multiple-core processors and massively parallel, high-density computing devices. Optionally, image reconstruction can also be performed on the processor 128 in the operator workstation 122. Reconstructed images can then be communicated back to the data store server 130 for storage or to the operator workstation 122 to be displayed to the operator or clinician.

The C-arm x-ray imaging system 100 may also include one or more networked workstations 148. By way of example, a networked workstation 148 may include a display 150; one or more input devices 152, such as a keyboard and mouse; and a processor 154. The networked workstation 148 may be located within the same facility as the operator workstation 122, or in a different facility, such as a different healthcare institution or clinic.

The networked workstation 148, whether within the same facility or in a different facility as the operator workstation 122, may gain remote access to the data store server 130, the image reconstruction system 132, or both via the communication system 134. Accordingly, multiple networked workstations 148 may have access to the data store server 130, the image reconstruction system 132, or both. In this manner, x-ray data, reconstructed images, or other data may be exchanged between the data store server 130, the image reconstruction system 132, and the networked workstations 148, such that the data or images may be remotely processed by the networked workstation 148. This data may be exchanged in any suitable format, such as in accordance with the transmission control protocol (TCP), the Internet protocol (IP), or other known or suitable protocols.

Figure 2C:
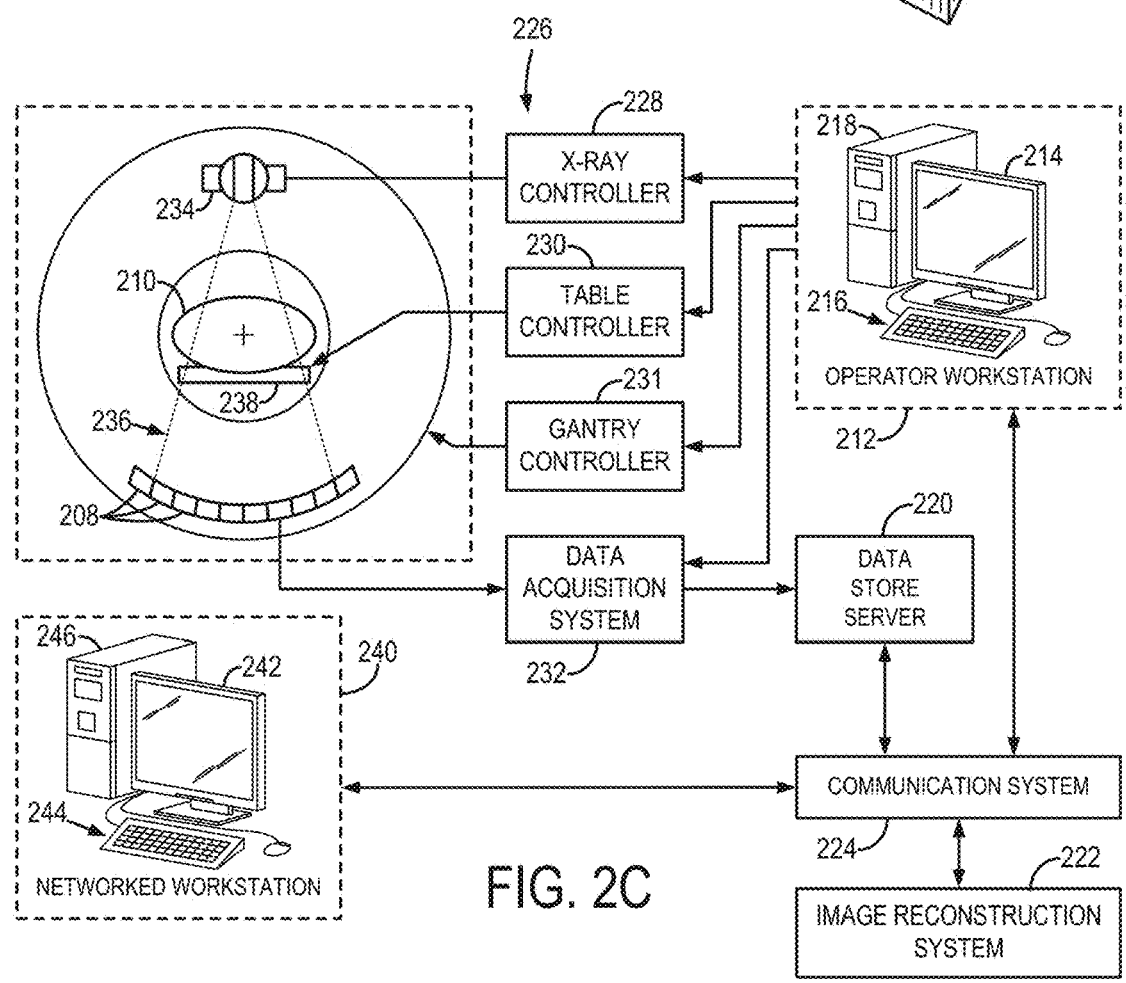
FIG. 2C is a block diagram of CT system, such as illustrated in FIG. 2B.

Similarly, referring to FIG. 2B and 2C, the imaging system 12 may include a traditional CT system 200, which includes a gantry 202 that forms a bore 204 extending therethrough. In particular, the gantry 202 has an x-ray source 206 mounted thereon that projects a fan-beam, or cone-beam, of x-rays toward a detector array 208 mounted on the opposite side of the bore 204 through the gantry 202 to image the subject 210.

The CT system 200 also includes an operator workstation 212, which typically includes a display 214; one or more input devices 216, such as a keyboard and mouse; and a computer processor 218. The computer processor 218 may include a commercially available programmable machine running a commercially available operating system. The operator workstation 212 provides the operator interface that enables scanning control parameters to be entered into the CT system 200. In general, the operator workstation 212 is in communication with a data store server 220 and an image reconstruction system 222 through a communication system or network 224. By way of example, the operator workstation 212, data store sever 220, and image reconstruction system 222 may be connected via a communication system 224, which may include any suitable network connection, whether wired, wireless, or a combination of both. As an example, the communication system 224 may include both proprietary or dedicated networks, as well as open networks, such as the Internet.

The operator workstation 212 is also in communication with a control system 226 that controls operation of the CT system 200. The control system 226 generally includes an x-ray controller 228, a table controller 230, a gantry controller 231, and a data acquisition system (DAS) 232. The x-ray controller 228 provides power and timing signals to the x-ray module(s) 234 to effectuate delivery of the x-ray beam 236. The table controller 230 controls a table or platform 238 to position the subject 210 with respect to the CT system 200.

The DAS 232 samples data from the detector 208 and converts the data to digital signals for subsequent processing. For instance, digitized x-ray data is communicated from the DAS 232 to the data store server 220. The image reconstruction system 222 then retrieves the x-ray data from the data store server 220 and reconstructs an image therefrom. The image reconstruction system 222 may include a commercially available computer processor, or may be a highly parallel computer architecture, such as a system that includes multiple-core processors and massively parallel, high-density computing devices. Optionally, image reconstruction can also be performed on the processor 218 in the operator workstation 212. Reconstructed images can then be communicated back to the data store server 220 for storage or to the operator workstation 212 to be displayed to the operator or clinician.

The CT system 200 may also include one or more networked workstations 240. By way of example, a networked workstation 240 may include a display 242; one or more input devices 244, such as a keyboard and mouse; and a processor 246. The networked workstation 240 may be located within the same facility as the operator workstation 212, or in a different facility, such as a different healthcare institution or clinic.

The networked workstation 240, whether within the same facility or in a different facility as the operator workstation 212, may gain remote access to the data store server 220 and/or the image reconstruction system 222 via the communication system 224. Accordingly, multiple networked workstations 240 may have access to the data store server 220 and/or image reconstruction system 222. In this manner, x-ray data, reconstructed images, or other data may be exchanged between the data store server 220, the image reconstruction system 222, and the networked workstations 212, such that the data or images may be remotely processed by a networked workstation 240. This data may be exchanged in any suitable format, such as in accordance with the transmission control protocol (TCP), the Internet protocol (IP), or other known or suitable protocols.

Using the systems described above, systems and methods are provided to reconstruct volumetric scout CT images from the 2D, two-view projection scout radiographs. The volumetric information can then be used to improve a variety of imaging processes, such as 3D volumetric imaging performed with CT, MRI, or other imaging modalities. For CT imaging, the volumetric information created from only 2D, two-view projection scout radiographs can substantially increase clinical ability to provide accurate radiation dose estimates that can inform scanning parameter prescription and, thus, overcome limitations of automatic exposure control schemes in diagnostic CT.

An image estimate, $\hat{x}$, is defined as the image that maximizes the a posteriori conditional probability $P(x|y)$ given the measured line integral data $y \in \mathcal{Y}$, where $\mathcal{Y}$ denotes sinogram space. This is accomplished via the Bayes inference and solving an optimization problem given by $\hat{x} = \text{argmax } P(x|y) = \text{argmax } P(y|x)P(x)$. This method requires an explicit assumption about the a priori distribution $P(x)$, which is typically available in current clinical CT acquisition schemes. Alternatively, in statistical machine learning, instead of using an explicit assumption on the prior $P(x)$, the posterior distribution $P(x|y)$ is learned from the training data via a supervised learning process.

As will be described, systems and methods are provided to reconstruct volumetric CT images using projection measurements from two views, where not only the data sufficiency conditions are severely violated, but also the prior information $P(x)$ about the imaging object is not available or is limited. The two views may be acquired using a CT imaging system as 2D, two-view projection scout radiographs. The two views may be orthogonal. For example, the two views may be an A/P view and a lateral view. However, any views may be used and A/P and lateral are non-limiting examples. In the case of CT imaging, these volumetric images can be used as 3-dimesional radiograph localizers to accurately determine a radiologic path from any view angle in order to improve dose CT prescription, such as tube current modulation schemes.

Figure 3:
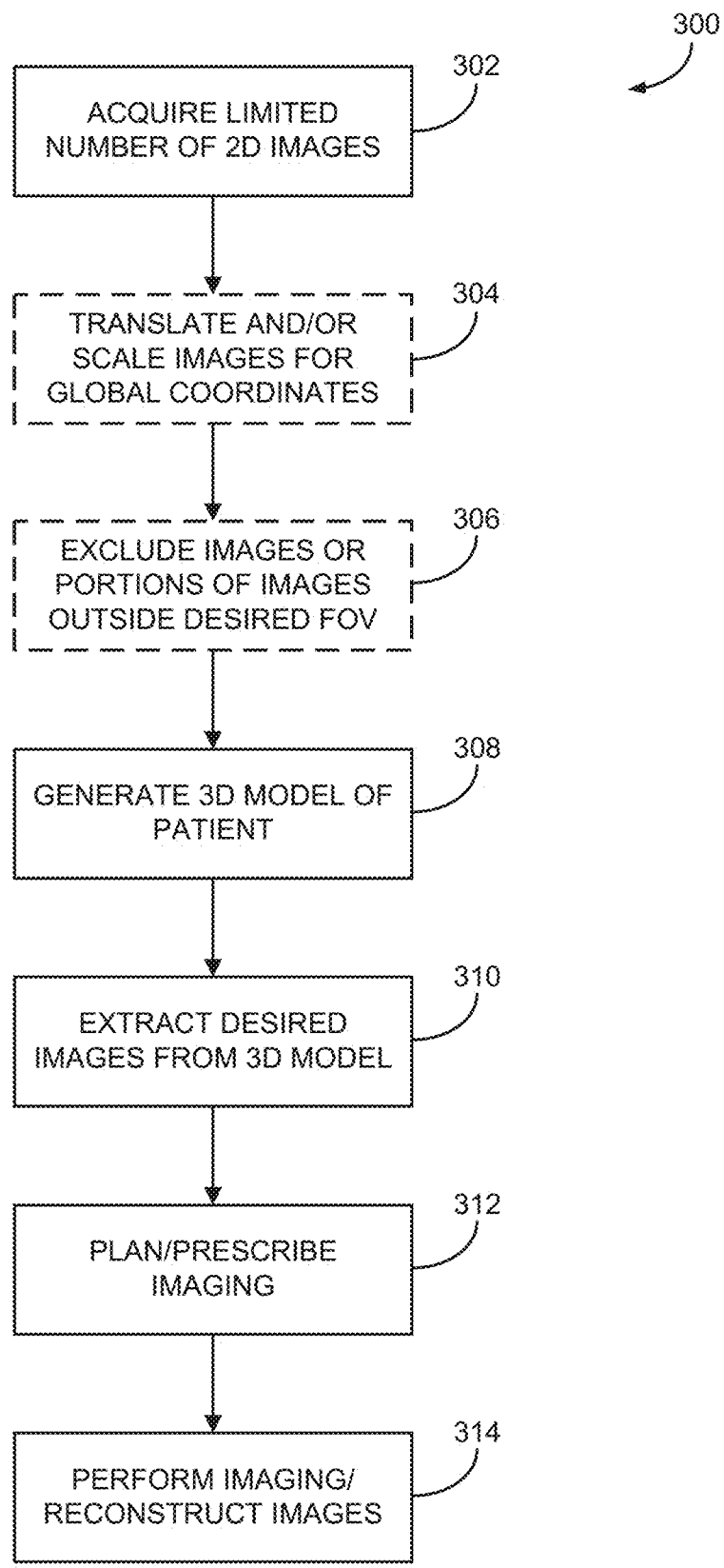
FIG. 3 is a block diagram of an image processing and/or reconstruction architecture in accordance with the present disclosure that may be utilized with or within the systems of FIGS. 1-2C and/or other imaging systems.

Referring to FIG. 3, one non-limiting example of a process 300 in accordance with the present disclosure is provided. At process block 302, the process 300 begins by acquiring a limited number (e.g., 2 or 3 or 4 or 5 or the like) S of 2D images, such as two images. For example, the images may be orthogonal radiograph localizers acquired using a CT system. In this case, the images may be antero-posterior (A/P) and lateral view localizers.

If the clinical imaging study involves the use of a contrast agent, the localizers may be acquired prior to the injection of intravenous (IV) or other contrast media. If contrast agents are utilized, the acquired images may be classified, for example, into four classes depending on the type of contrast media protocol: 1) IV, 2) oral contrast, 3) oral and IV, and 4) No contrast.

At optional process block 304, the acquired 2D images may be translated and/or scaled to match a set of global coordinates, for example, using an affine transformation. Such translation and/or scaling may account for differences in image reconstruction parameters, such as image thickness, voxel size and field of view position. In one non-limiting example implementation, a matrix size of 512×512 with 1.0×1.0×1.0 mm3 isotropic voxel size was used.

At optional process block 306, after each image in the dataset is within the global coordinate system, images where patient's anatomy is outside the reconstructed field of view (e.g. shoulders, subcutaneous fat, etc.) can be automatically excluded in order to avoid potential data inconsistency (i.e. reconstruction of data not present in the image).

At process block 308, the localizer images, which may be as few as two 2D images, are processed to create a 3D model of the patient. Specifically, given as set of line integrals $\{y_0, y_1, \ldots, y_N\}$ (input), measured over the distribution of attenuation coefficients of the imaging object represented by x (output), the process 300 at process block 308 seeks to model the conditional probability $P(x|y_0, \ldots, y_N)$ for this purpose. To do so a combination of recurrent and convolutional neural networks can be used that take the measured line integrals from the 2D radiograph localizers as input and generates a reconstructed 3D image volume as an output.

The choice of neural network architecture can vary, for example, by analytical reconstruction methods such as filtered backprojection (FBP) or by backprojection (BP) without filtering step. Similar to FBP where a ramp kernel is applied globally to the projection data and the backprojection of single line integral measurements is a localized operation over image domain, the hidden state computed by a recurrent neural network (RNN) cell at each step models localized features in the reconstructed image, while recurrent connections allow every layer in the network to access the entire neighborhood of previously computed hidden states, as will be further explained.

At process block 310, the 3D model of the patient is processed to extract desired images that are then used at process block 312 for imaging planning/prescription. That is, despite acquiring only a limited set (e.g., 2 or 3 or 4 or 5, etc.) of 2D images at process block 302, the 3D model is used to extract any number of images at any desired view angle to facilitate image planning or prescription. In this way, at process block 314, an imaging process is performed according to the planning/prescription of process block 312 that can ensure proper anatomical views, while reducing, controlling, and/or minimizing the dose delivered to the patient.

Figure 4:
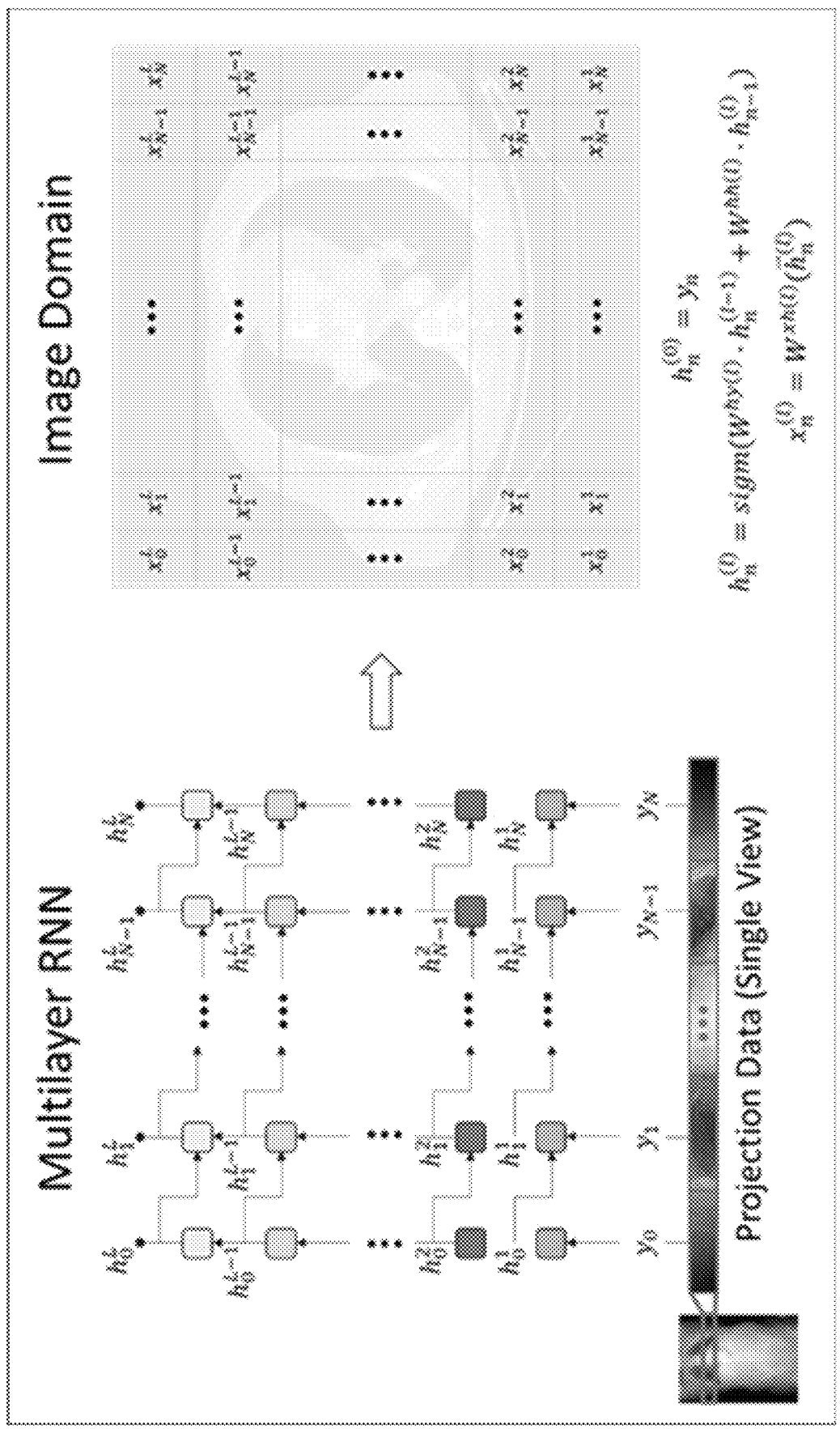
FIG. 4 is a graphical representation of a multilayer RNN for image reconstruction in accordance with the present disclosure.

As described above, a neural network architecture may be utilized, as illustrated in FIG. 4. Again, given as set of line integrals $\{y_0, y_1, \ldots, y_N\}$ (input), measured over the distribution of attenuation coefficients of the imaging object represented by x (output), a model the conditional distribution $P(x|y_0, \ldots, y_N)$ is sought. For this purpose, the target image x can be divided into smaller image tiles $\{x_0^1, \ldots, x_N^L\}$ and a sequence to sequence model can be used with a deep recurrent neural network to model $P(x_0^1, \ldots, x_N^L|y_0, \ldots, y_N)$. With a multilayer RNN, the output sequence $\{x_0^1, \ldots, x_N^L\}$ can be computed with the following equations:

$$h_n^{(0)} = y_n \qquad \text{Eqn. 1;}$$

$$h_n^{(l)} = \text{sigm}(W^{hy(l)} \cdot h_n^{(l-1)} + W^{hh(l)} \cdot h_{n-1}^{(l)}) \qquad \text{Eqn. 2;}$$

$$x_n^{(l)} = W^{xh(l)}(\vec{h}_n^{(l)}) \qquad \text{Eqn. 3;}$$

where $h_n^{(l)}$ represents the network hidden state at layer l and step n, $W^{hy(l)}$, $W^{hh(l)}$ and $W^{xh(l)}$ represents the input-to-hidden weights, hidden-to-hidden recurrent weights and the hidden-to-output weights respectively at layer l.

With this architecture, the chain rule can be used to factorize $P(x_0^1, \ldots, x_N^L|y_0, \ldots, y_N)$ as:

$$P(x_0^1, \ldots, x_N^L|y_0, \ldots, y_N) = \Pi_{l=1}^L \Pi_{i=0}^N P(x_n^l|y_0, \ldots, y_n) \qquad \text{Eqn. 4;}$$

where $P(x_n^l|y_0, \ldots, y_n)$ can be modeled with a softmax over the distribution of CT numbers (i.e. the probability of each voxel in the image taking the value of one of 4096 CT numbers for the typical dynamic range of a CT image, such as 12 bits). However, this approach can utilize a substantial amount of memory and computation while learning very slowly. Alternatively, given the continuous nature of the attenuation coefficients of the underlying imaging object, $P(x_n^l|y_0, \ldots, y_n)$ can be modeled with a logistic or Gaussian distribution.

While the previously-described method can be used, gated RNNs such LSTMs have been shown to outperform standard RNNs given their increased ability to model long-range temporal/spatial dependencies. Thus, a LSTM recurrent neural network can be used in which hidden states can be computed with the following equations:

$$h_n^{(l)} = o_n^{(l)} \cdot \tanh(s_n^{(l)}) \qquad \text{Eqn. 5;}$$

$$o_n^{(l)} = \sigma(W_o^{(l)} \cdot [h_{n-1}^{(l)}, h_n^{(l-1)}, y_n] + b_o^{(l)}) \qquad \text{Eqn. 6;}$$

$$s_n^{(l)} = f_n^{(l)} \cdot s_{n-1}^{(l)} + i_n^{(l)} \cdot \tilde{s}_n^{(l)} \qquad \text{Eqn. 7;}$$

$$\tilde{s}_n^{(l)} = \tanh(W_s^{(l)} \cdot [h_{n-1}^{(l)}, h_n^{(l-1)}, y_n] + b_s^{(l)}) \qquad \text{Eqn. 8;}$$

$$f_n^{(l)} = \sigma(W_f^{(l)} \cdot [h_{n-1}^{(l)}, h_n^{(l-1)}, y_n] + b_f^{(l)}) \qquad \text{Eqn. 9;}$$

$$i_n^{(l)} = \sigma(W_i^{(l)} \cdot [h_{n-1}^{(l)}, h_n^{(l-1)}, y_n] + b_i^{(l)}) \qquad \text{Eqn. 10;}$$

where the $W_o^{(l)}$, $b_o^{(l)}$, $W_s^{(l)}$, $b_s^{(l)}$, $W_f^{(l)}$, $b_f^{(l)}$ and $W_i^{(l)}$, $b_i^{(l)}$ represent the weights of the of the output gate $o_n^{(l)}$, cell state $s_n^{(l)}$, forget gate $f_n^{(l)}$ and input gate $i_n^{(l)}$ at layer l. $[h_{n-1}^{(l)}, h_n^{(l-1)}, y_n]$ represent a concatenation operation.

Figure 5:
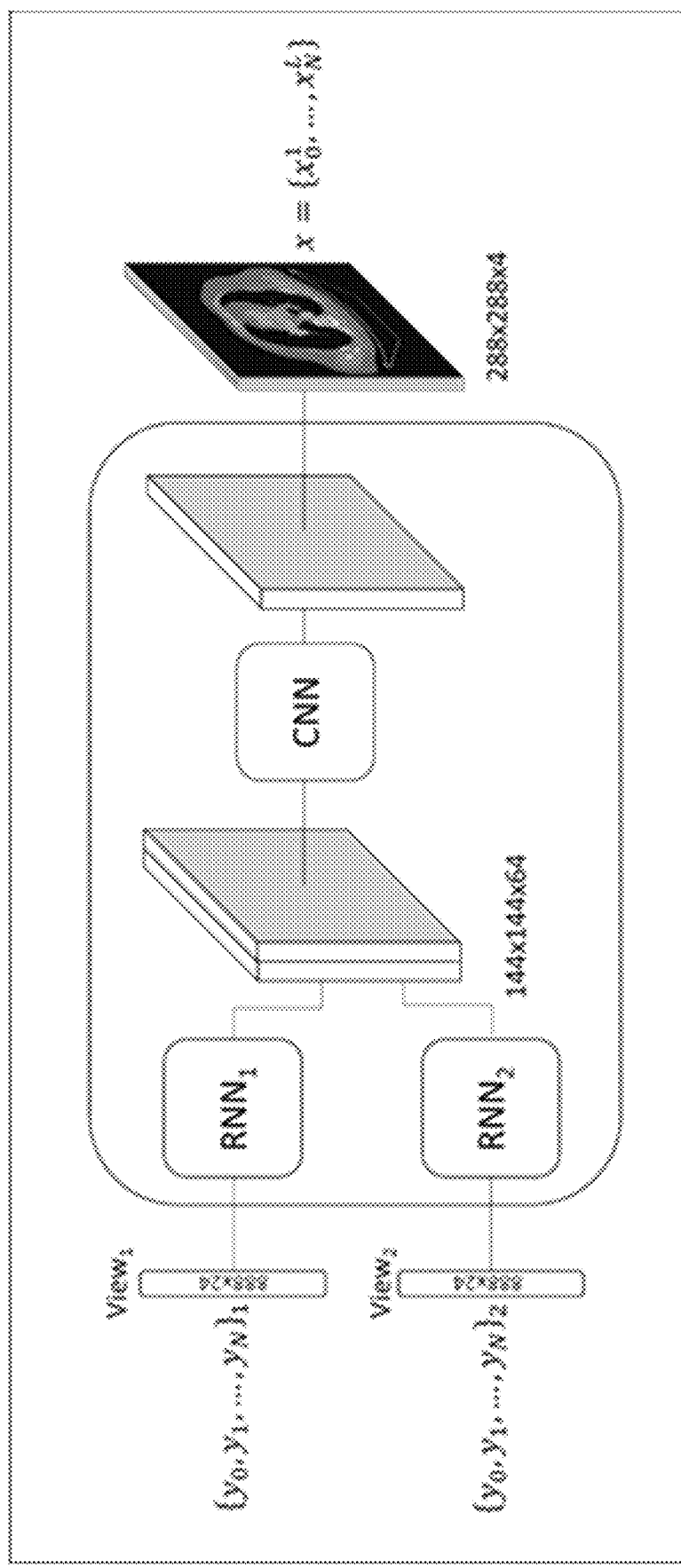
FIG. 5 is an illustration of an overall network framework including the multilayer RNN of FIG. 4 in accordance with the present disclosure.

The above-described architecture can use a single projection view as input. As illustrated in FIG. 5, in order to incorporate multiple views in the image reconstruction process, independent RNNs can be used for each view, and then the hidden states $h_n^{(l)}$ of each RNN can be concatenated. The resulting concatenated array is then processed by a CNN in order the compute the final image tiles $x_n^l$.

Figure 6:
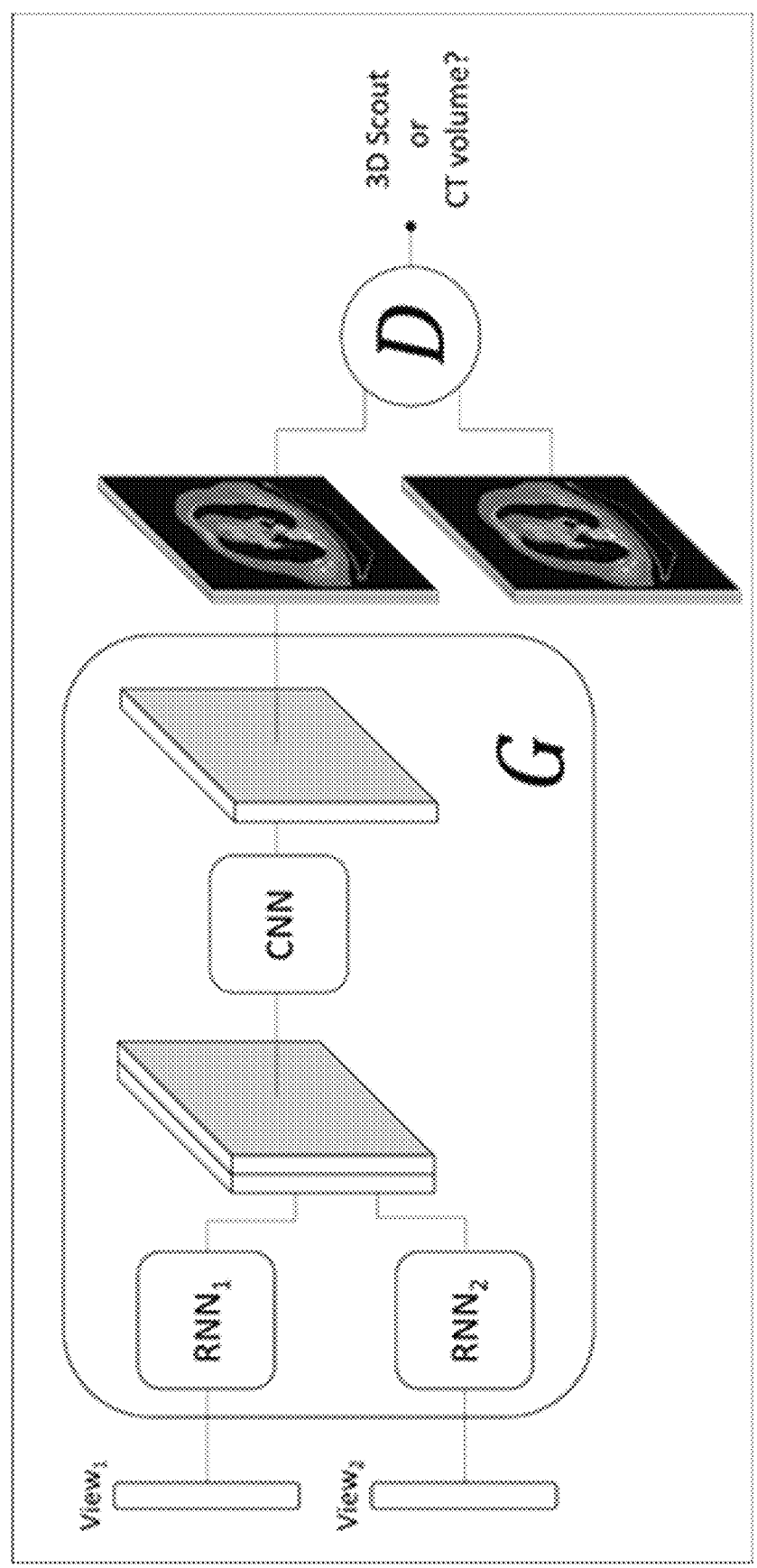
FIG. 6 is an illustration of an overall network framework including the multilayer RNN of FIG. 4 configured in an adversarial training scheme in accordance with the present disclosure.

The above-described architecture can be designed to reconstruct CT images of any matrix size. In one non-limiting example, two input projection views were used, each with size 888×24 and an image volume with size 288×288×4 was reconstructed. In this non-limiting example, the recurrent neural network had 9 layers that were computed for 144 steps (i.e., L=9 and N=[0,144)). For the CNN architecture that takes the concatenation of the hidden states of the RNN as input, a U-Net can be used. Rather than assuming a model for the underlying distribution $P(x_n^l|y_0, \ldots, y_n)$, an adversarial training strategy can be used where the above-described architecture is treated as the generator of a conditional GAN where a CNN with residual connections is used as the discriminator, as illustrated in FIG. 6. In this case, the objective function is regularized by the L1 distance of the reconstructed and target image. Therefore, the final objective is:

$$G^* = \arg\min_G \max_D \mathcal{L}_{GAN}(G, D) + \lambda \mathcal{L}_{L1}(G) \quad \text{Eqn. 11}$$

where $$\mathcal{L}_{GAN}(G, D) = \mathbb{E}_x[\log D(x)] + \mathbb{E}_y[\log(1 - D(G(y)))]$$

and $$\mathcal{L}_{L1}(G) = \mathbb{E}_{x,y}[\|x - G(y)\|_1].$$

Figure 7A:
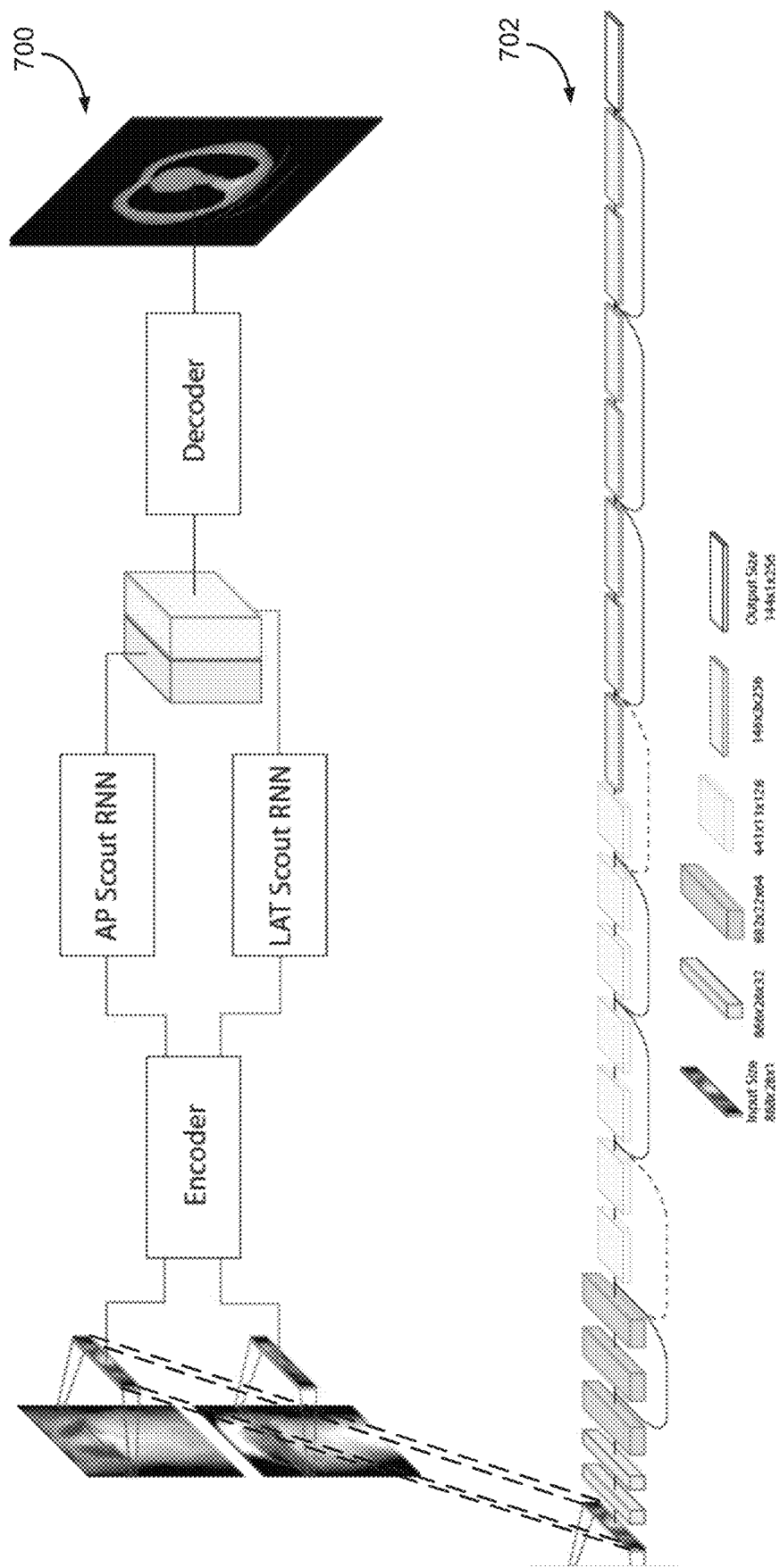
FIG. 7A is a schematic diagram of one, non-limiting implementation of a network framework in accordance with the present disclosure.
Figure 7B:
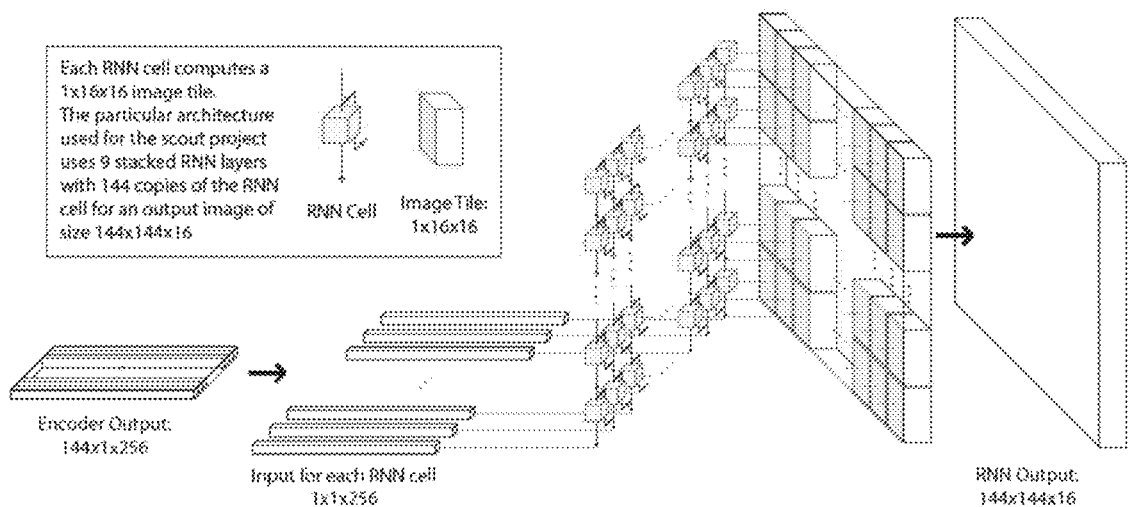
FIG. 7B is a schematic diagram of one, non-limiting implementation of a RNN Scout "back projection" architecture in accordance with the present disclosure.
Figure 7C:
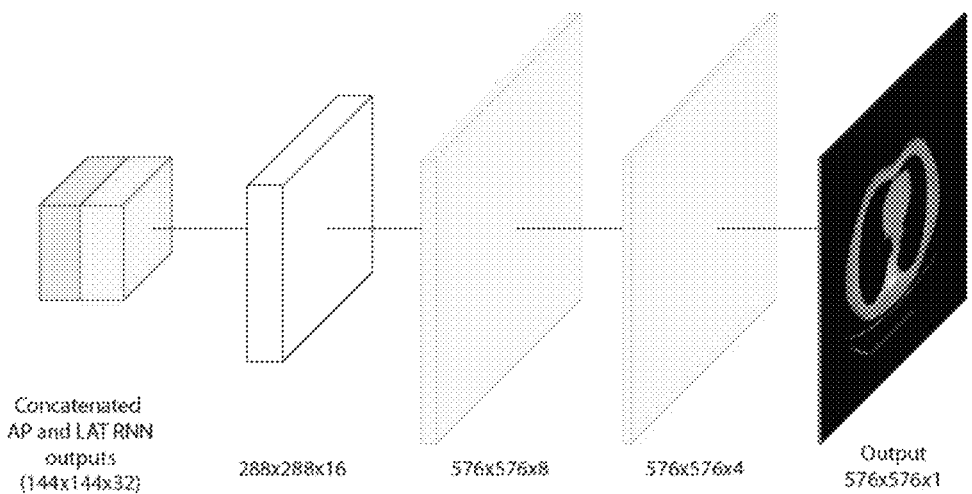
FIG. 7C is a schematic diagram of one, non-limiting implementation of a CNN images decoder in accordance with the present disclosure.

One implementation of the above-described network framework is illustrated in FIG. 7A. Specifically, FIG. 7A shows the above-described network framework 700 implemented using a non-limiting example of image and volume sizes to show the CNN scout encoder 702. As further shown in FIGS. 7B and 7C, non-limiting examples of an implementation of RNN Scout "back projection" (FIG. 7B) and CNN images decoder (FIG. 7C) are also provided.

EXAMPLE

In one non-limiting example study, clinical chest-abdomen-pelvis (CAP) CT exams from 667 patients were retrospectively collected. Inclusion criteria were as follow: 1) CT exams acquired with or without contras media (oral, IV or oral & IV) and 2) scanned with anatomical ranges in six different regions (chest alone, abdomen alone, pelvis alone, chest and abdomen, abdomen and pelvis or CAP). Only images reconstructed with a soft tissue kernel were included. After images were collected, to account for differences in image reconstruction parameters (i.e. FOV size and position, slice thickness, etc.) all CT image volumes were interpolated to a 1.0×1.0×1.0 mm³ isotropic voxel size. To control against potential data inconsistency, CT images where patient's anatomy was outside the image FOV were excluded (i.e. truncated CT images). Finally, the interpolated CT image volume were registered to the CT radiograph localizers using the patient's positioning information in the DICOM header. The resulting radiograph localizers and CT images were divided into training and testing datasets that were then used to train a 36-layer deep neural network, that takes as inputs the AP and lateral localizers and outputs a CT image volume with 1.0×1.0×1.0 mm³ isotropic voxel size. Once the deep neural network was trained, in order to test the generalization error of the model, the total patient attenuation was measured in a randomly selected subset of 1000 true CT and deep learning generated images for both the training and testing dataset and the absolute percent difference in total patient attenuation was calculated.

A total of 751 CT exams from 667 patients were included in the dataset for a total of 211,659 images. A deep neural network was trained using 163,840 images from 476 patients and tested using the remaining 47819 images from 191 patients. Mean and standard deviation for the total patient attenuation difference between the true CT and the deep learning generated images were 1.5±1.1% and 3.3±2.3% (n=1000 images) for the training and testing datasets.

A method to approximate the attenuation distribution of body cross-sectional CT images using the CT radiograph localizers was deployed. The method enabled accurate radiation dose estimates and image quality prescription prior to the CT acquisition and help to overcome the current limitations of automatic exposure control schemes in diagnostic CT.

By enabling accurate patient geometry and cross-sectional attenuation distribution estimations from the radiograph localizers acquired prior to the actual CT scan, the method provides a new way to conceptualize radiation dose and image quality prescription for diagnostic MDCT.

Figure 8:
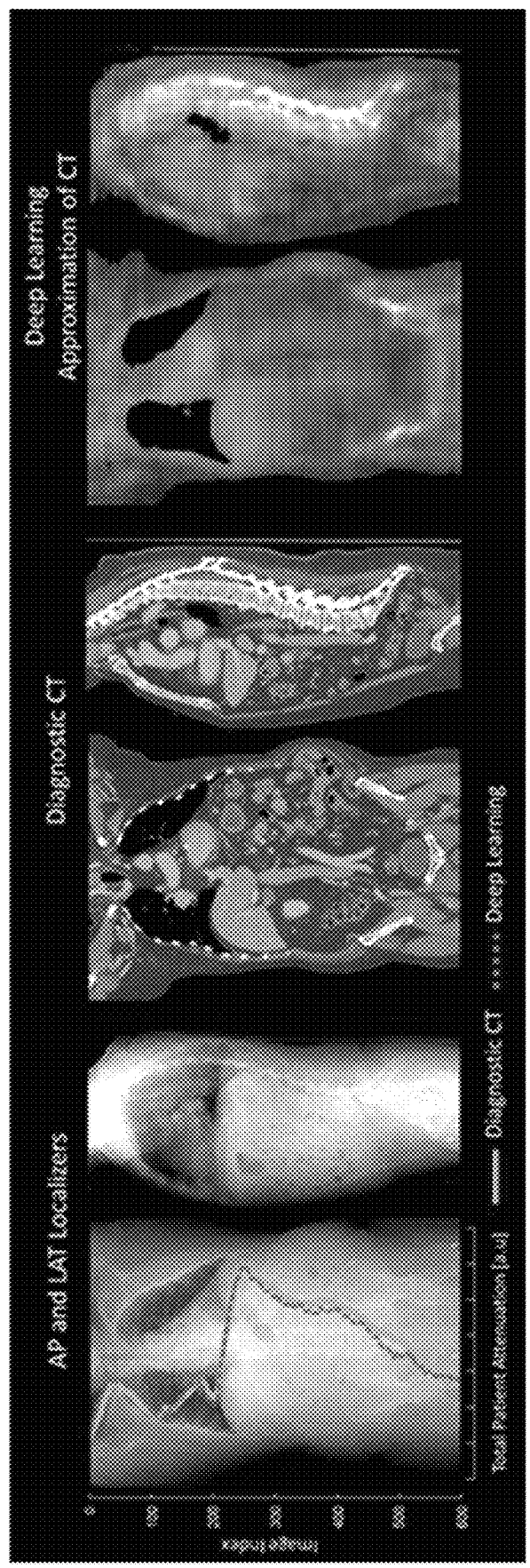
FIG. 8 is a series of images showing a comparison of coronal and sagittal images of a CAP CT exam for both a diagnostic CT and deep learning generated images together with a comparison of the total patient attenuation as a function of image index overlaid in the CT localizer image.
Figure 9:
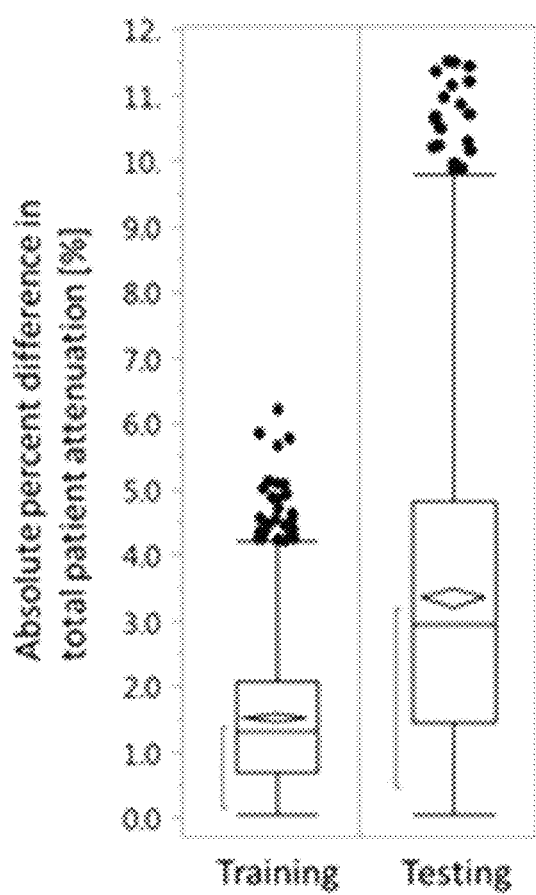
FIG. 9 is a box plot of the percent difference in total patient attenuation between the true CT and the proposed method, measured in a randomly selected subset of 1000 training and testing images.
Figure 10:
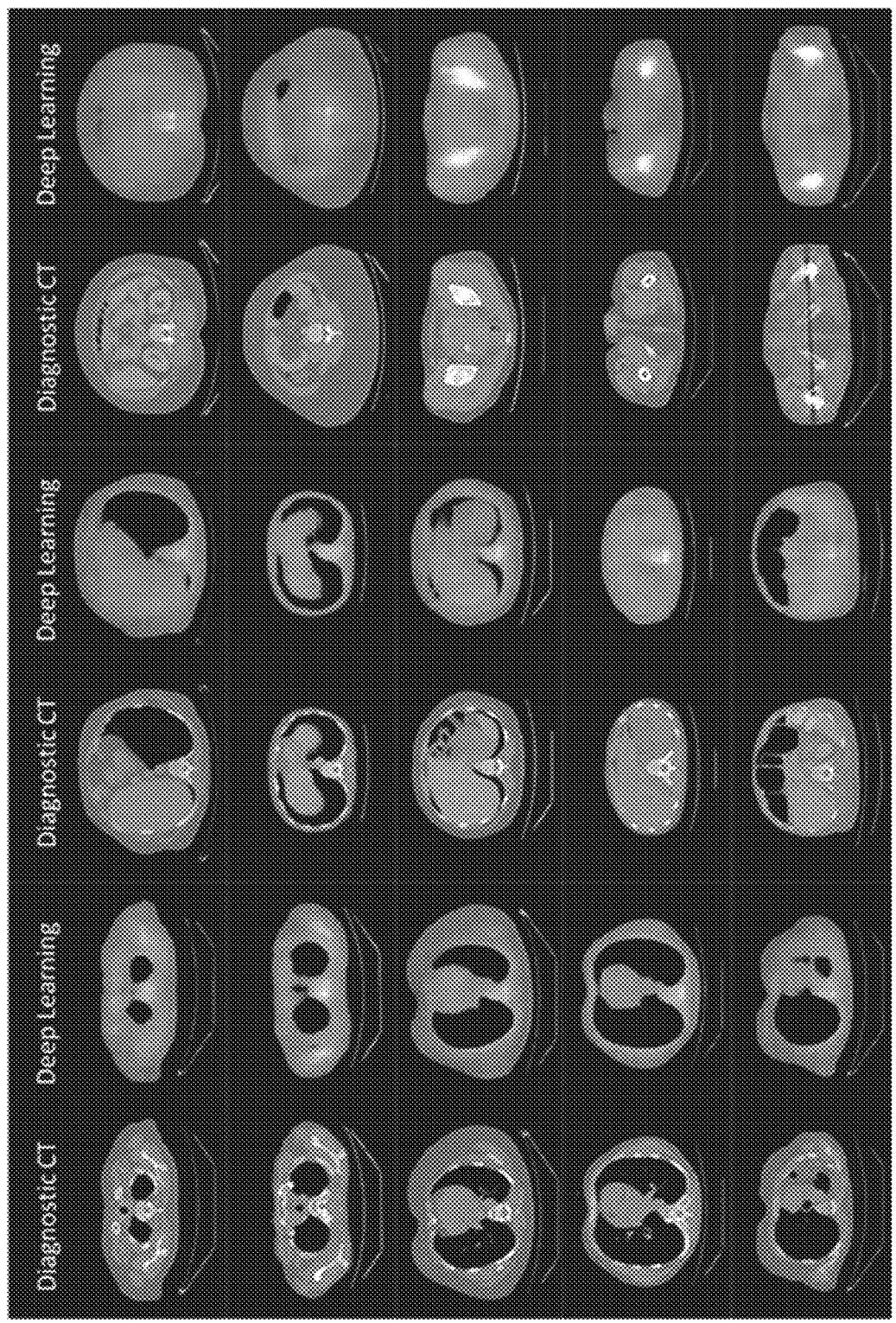
FIG. 10 is a series of images providing a side-by-side comparison of cross-sectional diagnostic CT and deep learning generated images for multiple anatomical regions ranging from the upper chest to the pelvis.

That is, the method can approximate a cross-sectional CT image from the CT radiograph localizers acquired prior to the actual the CT scan. It was found that the total patient attenuation measured in deep learning generated images, accurately approximated that of the true CT images with an absolute percent difference of 3.3±2.3% (n=1000 images). FIG. 8 shows a comparison of coronal sagittal images of a CAP CT exam for both a diagnostic CT and the deep learning generated images together with a comparison of the total patient attenuation as a function of image index overlaid in the CT localizer image. One can see that the total patient attenuation derived from the deep learning images closely approximates that of the actual CT scan. FIG. 9 shows a box plot of the percent difference in total patient attenuation between the true CT and the proposed method, measured in a randomly selected subset of 1000 training and testing images. FIG. 10 shows a side by side comparison of cross-sectional diagnostic CT and deep learning generated images in multiple anatomical regions for patients of various sizes. The deep learning images closely resemble the overall patient attenuation distribution in the diagnostic CT. There are some variations observed in the delineation of high-attenuation objects, such as bone. This behavior is expected given that only 2 views are used to create the deep learning images (i.e. AP and lateral radiograph localizers) prior to acquiring the actual CT scan.

Figure 11:
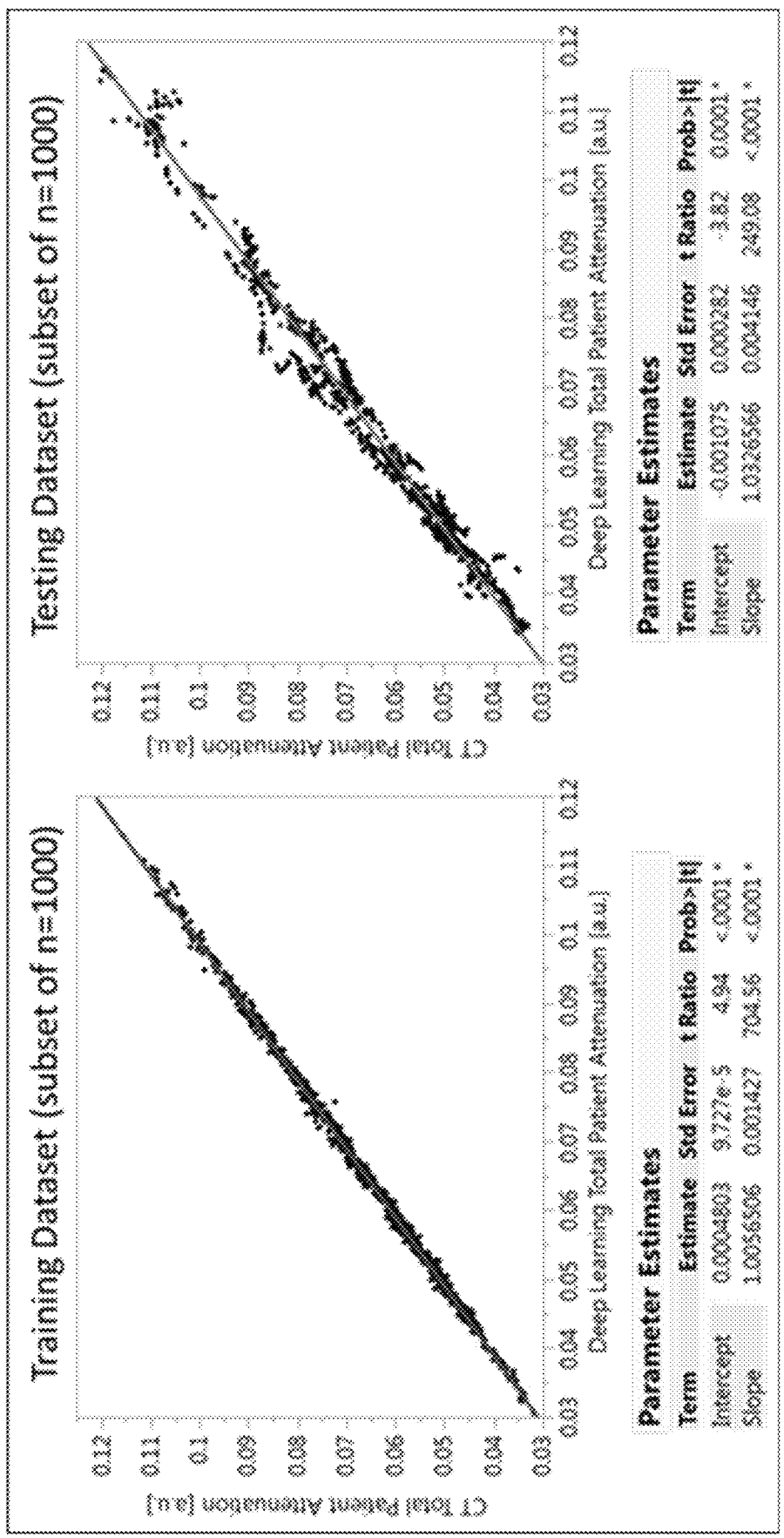
FIG. 11 is a set of linear plots of the total patient attenuation in CT images as function of the total patient attenuation measured in in the deep learning generated images for a randomly selected subset of 1000 images in both the training and testing dataset.

FIG. 11 shows linear plots of the total patient attenuation in CT images as function of the total patient attenuation measured in in the deep learning generated images for a randomly selected subset of 1000 images in both the training and testing dataset. Results indicate excellent linear relation between measurements derived from the diagnostic CT and deep learning images. Furthermore, the variability in the measurements appears to be constant across a wide range of patient sizes.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for acquiring medical images of a subject comprising:
    performing two-dimensional (2D) scout scan of a subject using a medical imaging system to acquire 2D data from at least two view angles;
    generating a three-dimensional (3D) model of the subject from the 2D data;

extracting desired images of the subject from the 3D model, wherein the desired images are at view angles different from the at least two view angles;

prescribing an imaging study of the subject using the desired images of the subject to control at least one of a signal-to-noise ratio of data acquired using the imaging study or a dose of ionizing radiation delivered to the subject during the imaging study;

performing the imaging study using the medical imaging system to acquire imaging data from the subject; and reconstructing images of the subject from the imaging data.

2. The method of claim 1 wherein the medical imaging system is a computed tomography (CT) imaging system.

3. The method of claim 1 wherein generating the 3D model of the subject form the 2D data includes providing the 2D data to a combination of at least one of recurrent and convolutional neural networks.

4. The method of claim 3 wherein the combination of at least one of recurrent and convolutional neural networks are configured to take measured line integrals from the 2D data as input and generates a reconstructed 3D image volume as an output to deliver the 3D model of the subject.

5. The method of claim 1 wherein the 2D scout scan include an anteroposterior (A/P) 2D image and lateral 2D image of the subject.

6. The method of claim 1 wherein the 2D scout scan include only 2 images.

7. A computed tomography (CT) system comprising:

an x-ray source and associated detectors configured to acquire imaging data from a subject over a range of view angles;

a computer system including at least one processor configured to:

cause the x-ray source and associated detectors to acquire two-dimensional (2D) localizer images of a subject at least two view angles;

generate a three-dimensional (3D) model of the subject from the 2D localizer images;

extract desired images of the subject from the 3D model, wherein the desired images are at view angles different from the at least two view angles;

prescribe an imaging study of the subject using the desired images of the subject to control a dose of ionizing radiation delivered to the subject by the x-ray source during the imaging study;

cause the x-ray source and associated detectors to perform the imaging study to acquire imaging data from the subject; and reconstruct images of the subject from the imaging data.

8. The system of claim 7 wherein generating the 3D model of the subject form the 2D localizer includes providing the 2D localizer to a combination of at least one of recurrent and convolutional neural networks.

9. The system of claim 8 wherein the combination of at least one of recurrent and convolutional neural networks are configured to take measured line integrals from the 2D localizer as input and generates a reconstructed 3D image volume as an output to deliver the 3D model of the subject.

10. The system of claim 7 wherein the 2D localizer images include an anteroposterior (A/P) 2D image and lateral 2D image of the subject.

11. The system of claim 7 wherein the 2D localizer images include only 2 images.

12. A method for acquiring medical images of a subject comprising:

acquiring two-dimensional (2D) fluoroscopic image series of a subject using a medical imaging system that acquires 2D projection data from at least two fluoroscopic units operated simultaneously during an imaging process;

generating a three-dimensional (3D) model from at least two of the 2D fluoroscopic image series at a given time point in the imaging process;

creating a 3D model for each remaining time point across the imaging process to generate a four-dimensional (4D) model;

extracting a motion profile from 4D model; and generating a treatment strategy, including subject positioning, using the 4D model.

13. A computed tomography (CT) system comprising:

an x-ray source and associated detectors configured to acquire imaging data from a subject over a range of view angles;

a computer system including at least one processor configured to:

cause the x-ray source and associated detectors to acquire two-dimensional (2D) images of a subject in at least two groups of two view angles, wherein one group of the at least two view angles is acquired at a lower tube potential and another group of the at least two view angles is acquired at a higher tube potential;

generate a first three-dimensional (3D) model of the subject from the 2D images using view angles acquired at the lower tube potential;

generate a second 3D model of the subject from the 2D images using view angles acquired at the higher tube potential;

combine the first and the second 3D models to a generate dual energy basis image volume;

extract desired spectral images of the subject from at least one of the first and the second 3D models, wherein the desired spectral images are at view angles different from the at least two view angles acquired at the lower tube potential or the at least two view angles acquired at the higher tube potential;

prescribe an imaging study of the subject using the desired images of the subject to control a dose of ionizing radiation to be delivered to the subject by the x-ray source during the imaging study;

cause the x-ray source and associated detectors to perform the imaging study to acquire spectral imaging data from the subject; and reconstruct spectral images of the subject from the spectral imaging data.

14. The system of claim 13 wherein generating the first 3D model or the second 3D model of the subject form the 2D images includes providing a 2D localizer to a combination of at least one of a recurrent or a convolutional neural networks.

15. The system of claim 14 wherein the combination of at least one of the recurrent or the convolutional neural networks are configured to take measured line integrals from the 2D localizer as input and generates a reconstructed 3D image volume as an output to deliver at least one of the first 3D model or the second 3D model of the subject.

16. The system of claim 14 wherein the 2D localizer is configured to generate images that include an anteroposterior (A/P) 2D image or lateral 2D image of the subject.

17. The system of claim 13 wherein the 2D images include only 2 images for each tube potential.

* * * * *